United States Patent
Chern et al.

[11] Patent Number: 5,885,256
[45] Date of Patent: Mar. 23, 1999

[54] SAFETY SYRINGE WITH A NEEDLE RECEIVING TUBE

[75] Inventors: Jinq-Shing Chern, No. 25, 10 Lin, Nan Shih Chun, Lin Kao Hsiang; Yuh-Lin Han, both of Taipei Hsien, Taiwan

[73] Assignee: Jinq-Shing Chern, Hsien, Taiwan

[21] Appl. No.: 56,740

[22] Filed: Apr. 8, 1998

[51] Int. Cl.$^6$ .............................. A61M 5/32; A61M 5/00
[52] U.S. Cl. ..................... 604/192; 604/110; 604/240
[58] Field of Search ..................... 604/110, 192, 604/195, 181, 187, 218, 228, 240, 241, 242, 243, 199, 263

[56] References Cited

U.S. PATENT DOCUMENTS

| | | | |
|---|---|---|---|
| 4,883,471 | 11/1989 | Braginetz et al. | 604/195 |
| 5,098,402 | 3/1992 | Davis | 604/195 |
| 5,242,401 | 9/1993 | Colsky | 604/110 |
| 5,273,543 | 12/1993 | Bell et al. | 604/110 |
| 5,554,126 | 9/1996 | Filley | 604/192 |
| 5,634,903 | 6/1997 | Kurose et al. | 604/110 |
| 5,687,740 | 11/1997 | Sheridan | 128/760 |
| 5,688,240 | 11/1997 | Novacek et al. | 604/110 |

*Primary Examiner*—Wynn Wood Coggins
*Assistant Examiner*—Michael J. Hayes
*Attorney, Agent, or Firm*—Bacon & Thomas

[57] ABSTRACT

A safety syringe is particularly equipped with a needle receiving tube which safely facilitates the mounting and dismounting of a disposed needle. The safety syringe has a container, an injection rod, a needle and a needle receiving tube. The needle can be withdrawn into the container via rotation of the injection rod after being used for disposal so as to protect hospital personnel from being accidentally punctured by a disposed needle which can cause fatal contagion of various diseases. The container is provided with a protruded needle mounting neck having a lid attached to the edge thereof. The injection rod housed in the container has a rubber piston head which is provided with a plunger end. The plunger end is made up of 4 symmetric plane extensions each having a round projection on the edge of each plane extension. The needle has a slantly cut shot end and a threaded engagement bottom end which is internally provided with 4 symmetric plane lugs and a protruded ring at the edge thereof for retaining purpose. The plunger end of the injection rod can firmly engage with the bottom end of the needle in the mounting and dismounting of a needle housed in a needle receiving tube so as to protect a hospital personnel from being accidentally punctured by a disposed needle.

3 Claims, 8 Drawing Sheets

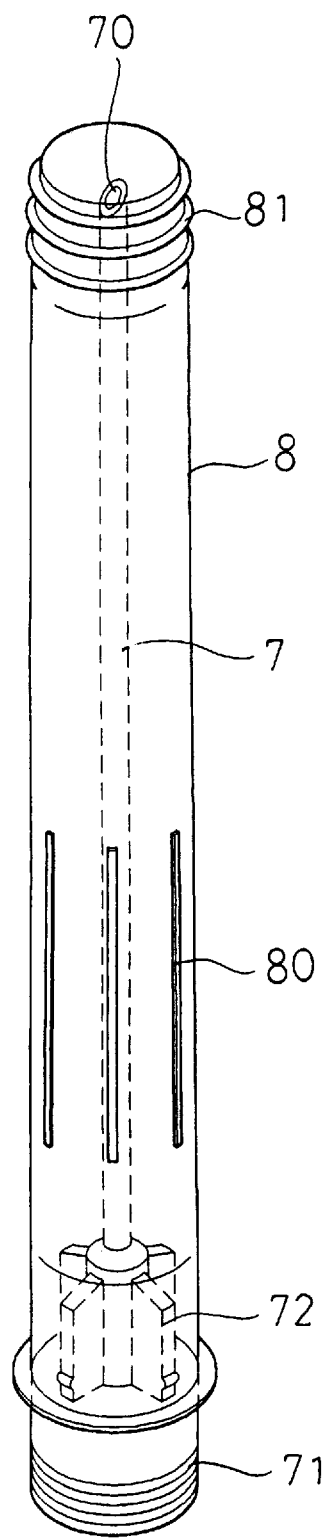
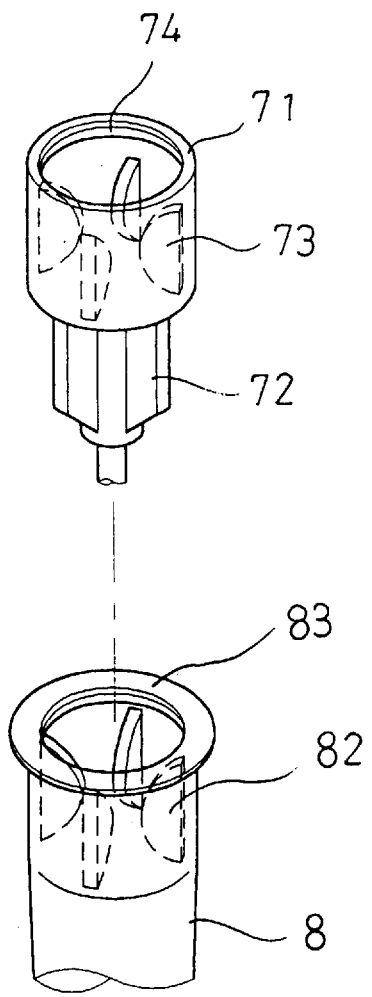
FIG. 5
FIG. 5A

SAFETY SYRINGE WITH A NEEDLE RECEIVING TUBE

BACKGROUND OF THE INVENTION

The present invention relates to a safety syringe particularly equipped with a needle receiving tube which safely facilitates the mounting and dismounting of a disposed needle. The safety syringe has a container, an injection rod, a needle and a needle receiving tube. The needle can be withdrawn into the container via rotation of the injection rod after being used for disposal so as to protect hospital personnel from being accidentally punctured by a disposed needle which can cause fatal contagion of various diseases. The container is provided with a protruded needle mounting neck having a lid attached to the edge thereof. The injection rod housed in the container has a rubber piston head which is provided with a plunger end. The plunger end is made up of 4 symmetric plane extensions each having a round projection on the edge of each plane extension. The needle has a slantly cut shot end and a threaded engagement bottom end which is internally provided with 4 symmetric plane lugs and a protruded ring at the edge thereof for retaining purpose. The plunger end of the injection rod can firmly engage with the bottom end of the needle in the mounting and dismounting of a needle housed in a needle receiving tube so as to protect a hospital personnel from being accidentally punctured by a disposed needle.

There have been many hospital related personnel suffering from fatal contagion of various diseased as a result of accidentally punctured by disposed needles, such as AIDS, TB and diseases of the like, which are distributed via blood. So, it is a life and death matter for doctors and nurses to deal with disposed needles within hospitals and clinics.

To better protect hospital personnel from being fatally punctured by disposed needles, a number of safety syringes have been designed and marketed for many years. The most common safety syringes on markets are made up of more than 4 pieces, causing the production cost of syringes to increase in one aspect and to burden the natural enviroment when disposed without processing in another aspect. So, it is not popularly used at all.

Furthermore, another type of safety syringe as illustrated in FIGS. 1, 2, such a prior art safety syringe is made up of a tubular container 1, an injection rod 2, a needle 3 and a needle cover (not shown). The tubular container 1 has a needle mount 10 for the retaining of the needle 3 at one end and has an oval shaped stop flange 11 at the other end. A limiting plate 12 having a retaining recess 13 at its edge extends from one side of the stop flange 11. The injection rod 2 having a cross-shaped section is slidably housed in the tubular container 1. At the front end of the injection rod 2 is disposed a piston end 20 having a mushroom-shaped retaining piece 21 at one end and at the other end of the injection rod 2 is disposed a circular disk 22. On two opposite points of the periphery of the circular disk 22 are disposed a retaining piece 23 respectively which is engaged with the retaining recess 13 of the limiting plate 12 of the tubular container 1.

The needle 3 has a slantly cut puncturing end 30 and the other end of the needle 3 has an outerly threaded tube 31 having a pair of opposite openings on the wall thereof. There are two slant retaining claws 32a, 32b housed in the threaded tube 31 and extending from the edge of the openings respectively, as shown in FIG. 1, so as to permit the mushroom shaped retaining piece 21 to be locked in place by the retaining claws 32a, 32b. The slant angles of the retaining claws 32a, 32b are not identical. When the injection rod 2 is pulled backward, the needle 3 can be withdrawn into the tubular container 1 after the needle 3 is rotated to disengage from the needle mount 10. The needle will lean to one side as a result of the difference of the slant angles of the retaining claws 32 when it is pulled into the tubular container 1. Afterwards, the needle mount 10 is closed by the needle cover (not shown) so as to protect hospital personnel from being pricked by disposed needles which are withdrawn into the tubular container after use.

Such a prior art safety syringe has the following disadvantages in its design and practical use:
1. The needle is easily subject to contamination after it is taken out from its germ-free packing by hospital personnel wearing no gloves and exposed to the air.
2. The needle cover is easily dropped and the exposed needle can get people pricked accidentally.
3. The retaining claws are made in a relatively complex manner having too many cuts and corners in which residues produced in a manufacturing process can be hidden and injected into a patient's body via blood vessels, causing unexpected diseases.
4. The injection rod can not be pushed fully to the bottom end of the tubular container, making medical liquids unable to be fully and efficiently injected into patients' bodies.
5. The tubular container is not provided with slippery proof strips; a person exerting a large force to withdraw the injection rod and get a disposed needle pulled into the tubular container will easily get pricked by a used needle as a result of slippery of his or her hands off the tubular container.

SUMMARY OF THE INVENTION

Therefore, the primary object of the present invention is to provide a safety syringe with a needle receiving tube in which a pointed needle is housed. The needle can be mounted to a syringe container with the needle safely housed in the needle receiving tube and the needle after injection can be withdrawn into the injection container of the syringe by way of rotation with the needle receiving tube attached to the needle for completely guarding people from being accidentally pricked by a used needle Another object of the present invention is to provide a safety syringe with a needle receiving tube which has less components and is produced at a lower cost each piece so that the safety syringe can be accepted and marketed with ease.

BRIEF DESCRIPTION OF THE DRAWINGS

FIG. 5 is a diagram showing the location of the needle in a needle receiving tube;

FIG. 5A is a partial diagram showing the detailed structure of the ends of the needle and the needle receiving tube;

DETAILED DESCRIPTION OF THE PREFERRED EMBODIMENT

Figure 1:
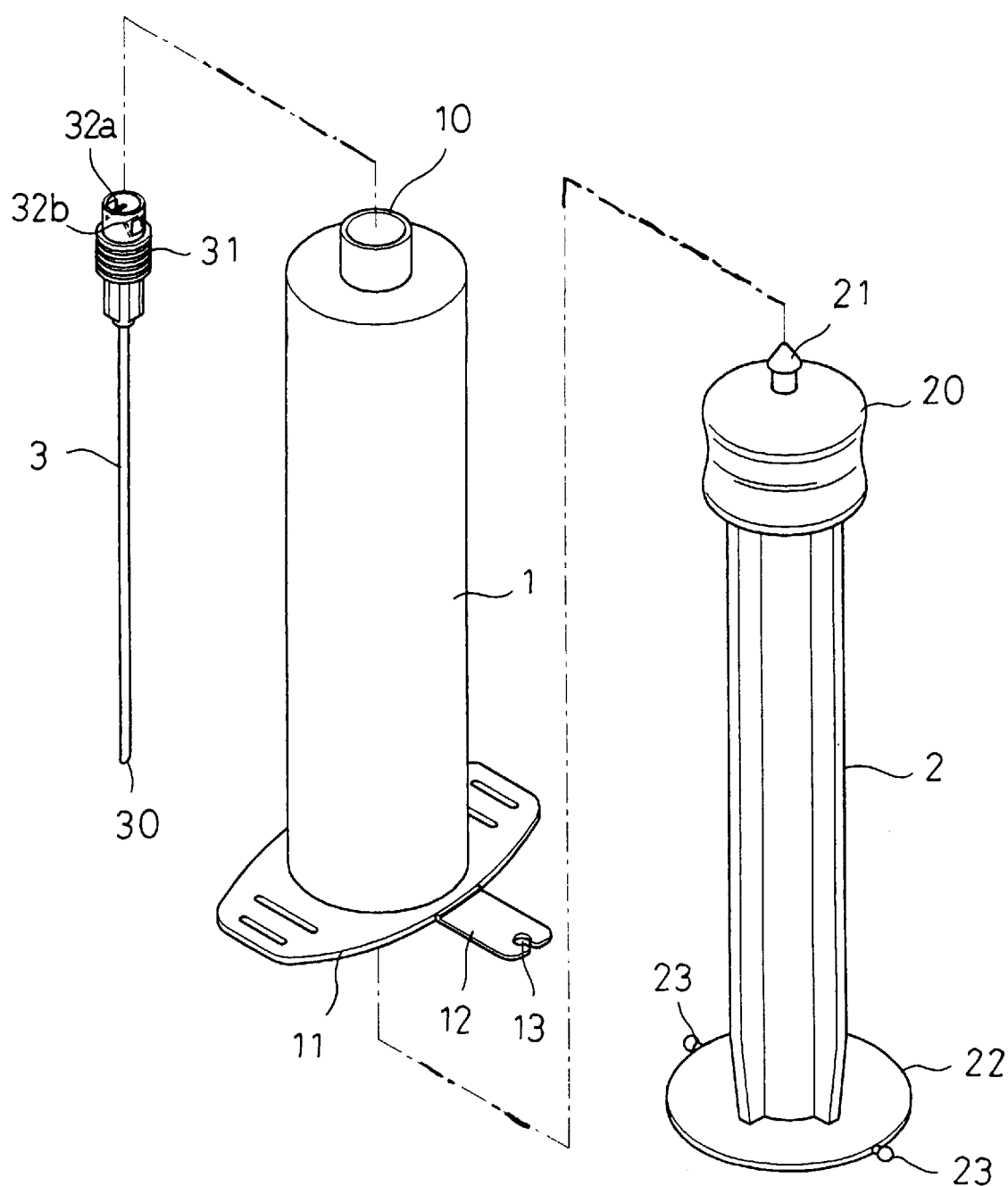
FIG. 1 is a perspective diagram showing the exploded components of a most commonly used syringe.
Figure 2:
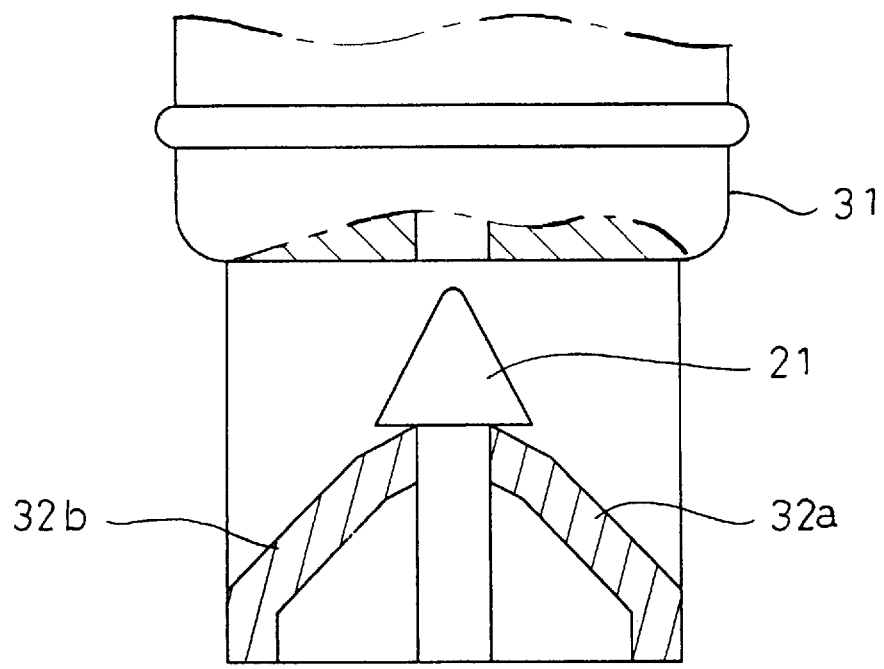
FIG. 2 is a sectional diagram showing the operation mode of the prior art syringe shown in FIG. 1.
Figures 3, 4A:
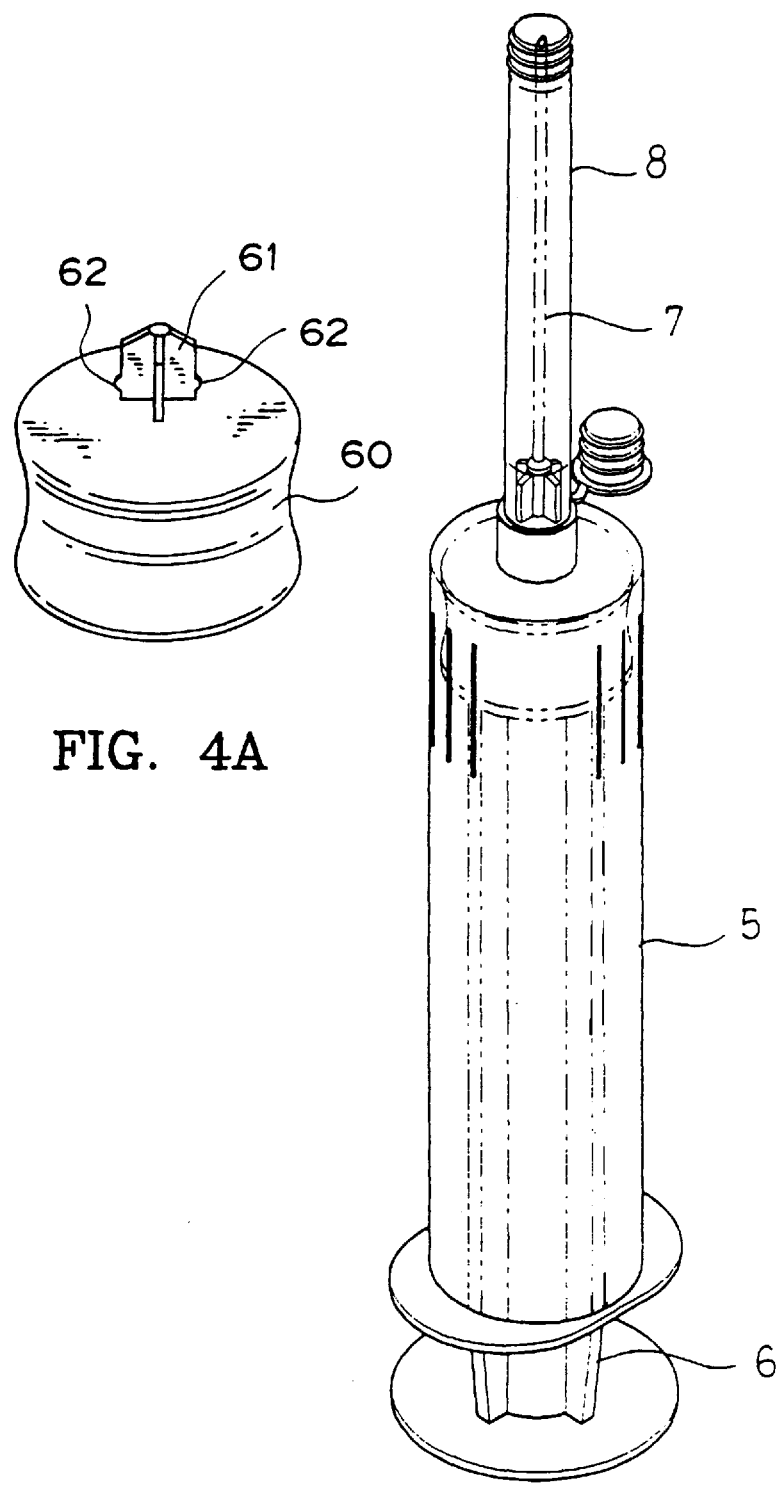
FIG. 3 is a perspective diagram showing the mounting of a needle of the safety syringe of the present invention.
FIGS. 4 and 4a are perspective diagrams showing the exploded components of the present invention.
Figure 4:
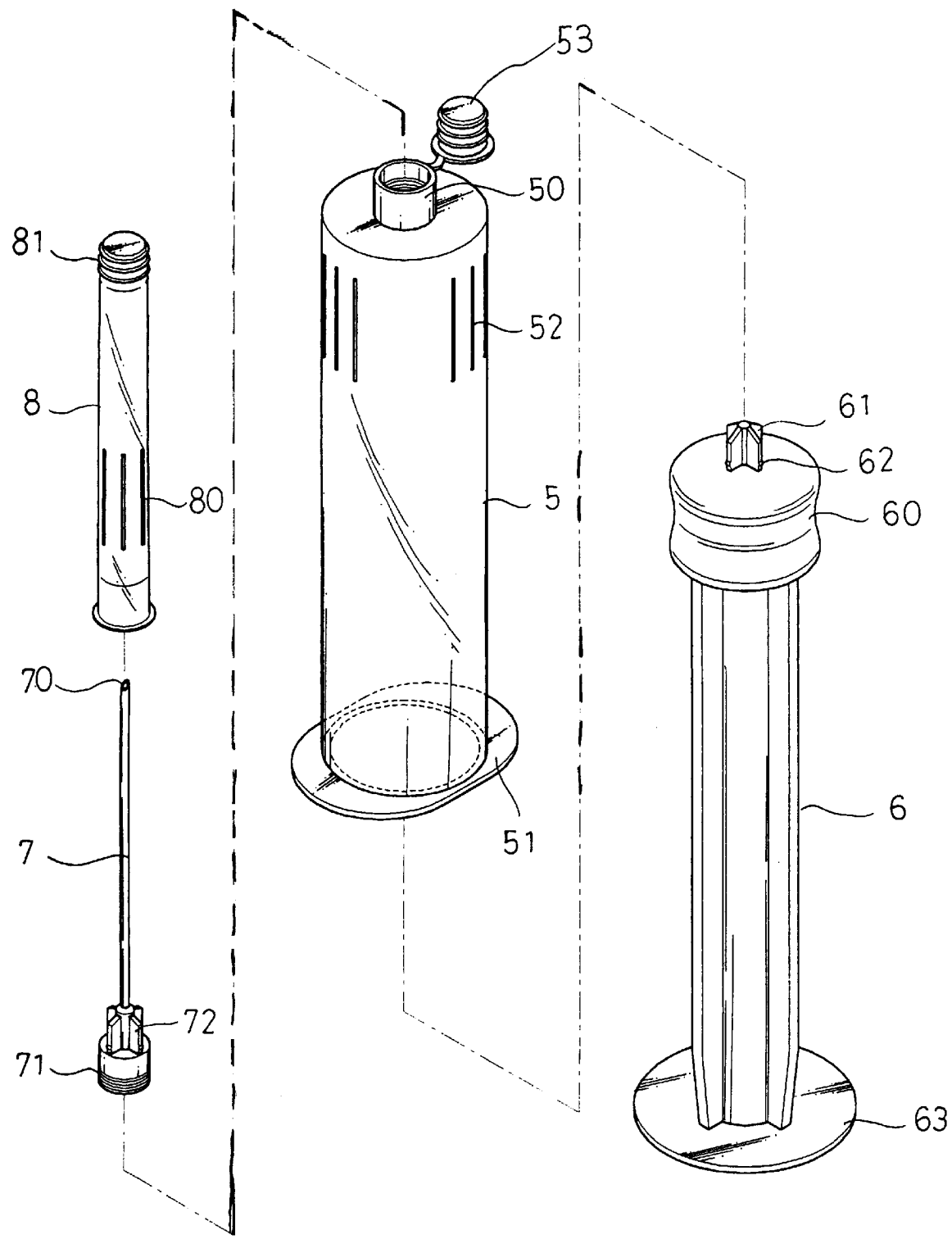

Referring to FIG. 4, the safety syringe of the present invention is comprised of a tubular container 5, an injection rod 6, a needle 7 and a needle receiving tube 8.

The features or characteristics of the safety syringe of the present invention are given in the following accounts of the structure thereof. The tubular container 5 has a protruded needle mounting neck 50 at one end and a holding flange 51 at the other end. There are a plurality of axially extended anti-slip linear protrusions 52 disposed on the outer surface of the tubular container 5 so as to permit a person to firmly hold the container 5 without slip when pulling the injection rod 6 outwardly. The protruded needle mounting neck 50 is provided with a lid 53 attached to the edge of the needle mounting neck 50 and a threaded inner wall for the securing of the needle 7.

The injection rod 6 has a cross-shaped sectional figure. It can be designed to have a triangle, rectangle or hexagon-shaped sectional figure too. At one end of the injection rod is disposed a rubber piston head 60. The rubber piston head 60 is provided with a plunger end 61 having a cross-shaped figure. The plunger end 61 has 4 vertical planes perpendicular to each other and at the edge of each plane is provided with a projected spot 62. At the other end of the injection rod 6 is provided with a round disc 63 for easy operation of the injection rod 6.

The needle 7 has a slantly cut injection hole 70 at one end and another externally threaded cylindrical mounting end 71 which is engaged with the needle mounting neck 50 of the tubular container 5 in assembly. At the top of the cylindrical mounting end 71 is disposed a protruded block 72 in the same shape as the plunger end 61 having a cross-shaped figure made up of 4 vertical planes orthogonal to each other. So, the needle 7 can be fixed in place in the needle receiving tube 8 without moving or shaking randomly.

Referring further to FIG. 5A, the externally threaded cylindrical mounting end 71 is provided with 4 symmetrically disposed semi-circular lugs 73 on the inner wall thereof. The cylindrical mounting end 71 has a protruded ring 74 adjacent to the edge of the mounting end 71. The semi-circular lugs 73 defined in the interior of the mounting end 71 are arranged in such a manner that the cross-shaped plunger end 61 of the piston head 60 of the injection rod 6 can just fit in with the cylindrical mounting end 71.

The needle receiving tube 8 has a slightly tapered shape and is equipped with a plurality of linear protrusions 80 in the longitudinal direction. The receiving tube 8 has an opened bottom end and a closed top end which is solid and is provided with a continuous spiral rib 81 for engagement with the needle mounting neck 50 of the tubular container. A peripheral flange 83 is disposed at the opened bottom end 83 and in the receiving tube 8 and right above the flange 83 are disposed 4 symmetric semi-circular lugs 82.

Referring to FIG. 3, to mount a fresh needle 7 housed in the needle receiving tube 8 onto the tubular container 5, the opened end of the needle receiving tube 8 is attached to the needle mounting neck 50 and the plunger end 61 of the injection rod 6 is forced into engagement with the cylindrical mounting end 71 of the needle 7 and then the injection rod 6 is rotated continually until the needle 7 is secured by way of its threads to the needle mounting neck 50 of the tubular container 5. After the needle 7 is secured in place to the container 5, the needle receiving tube 8 is then removed to expose the secured needle for use.

Figures 6A, 6B, 6C:
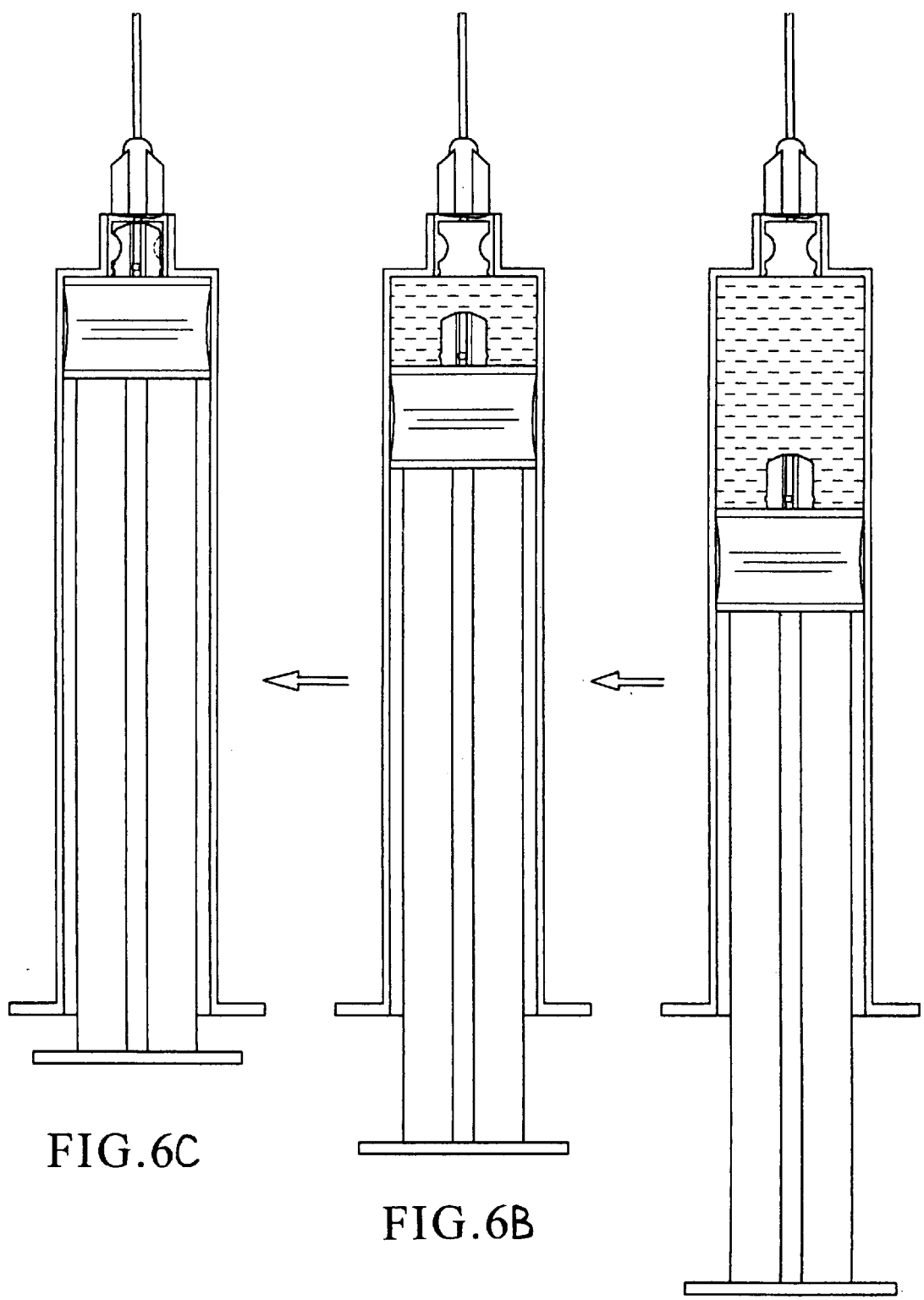
FIGS. 6A, 6B and 6C are serial diagrams showing the operation of the injection rod in the container of the safety syringe of the present invention.
Figure 7:
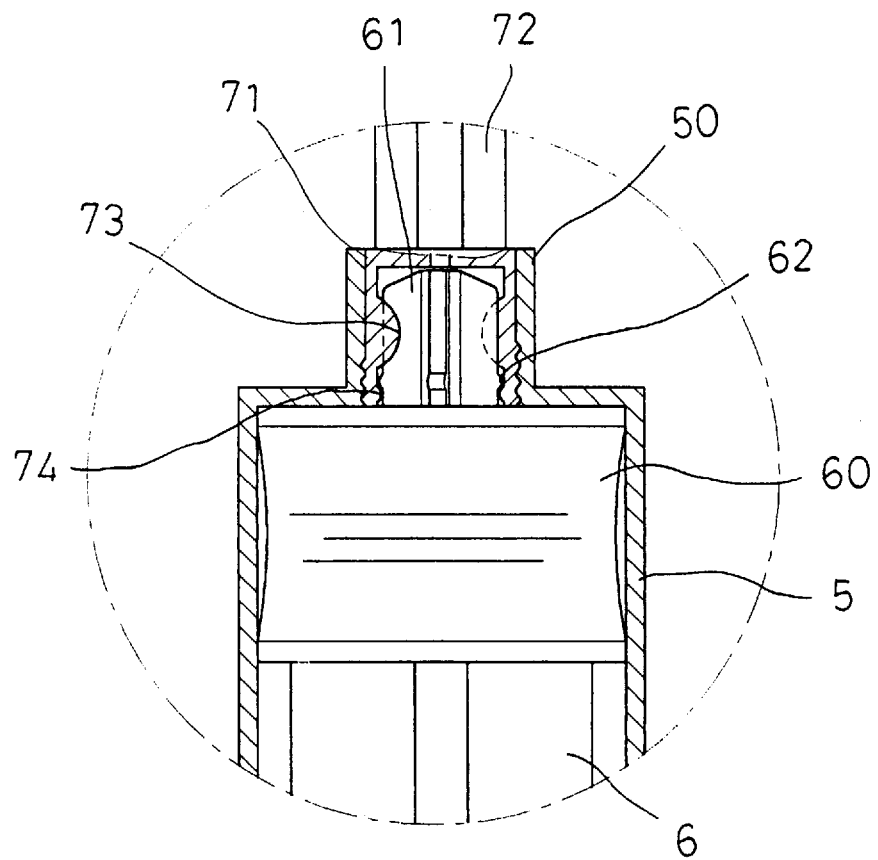
FIG. 7 is an enlarged diagram showing the detailed engagement of the plunger end of the injection rod with the bottom end of the needle.

As shown in FIGS. 6A, 6B, 6C, when the liquid medicine in the safety syringe runs out through injection step by step and the person engaging in the shot is going to dispose the tubular container, he or she will hold the container 5 with the left hand and continue pushing the injection rod 6 with the right hand by way of the round disc 63, causing the plunger end 61 of the rubber piston head 60 to engage with the mounting end 71 of the needle 7. The 4 symmetric vertical planes of the cross-shaped plunger end 61 are limited by the 4 symmetric semi-circular lugs 73 with the projected spots 62 retained in place by the protruded ring 74 at the same time, as shown in FIG. 7.

Figures 8, 8A, 8B, 8C:
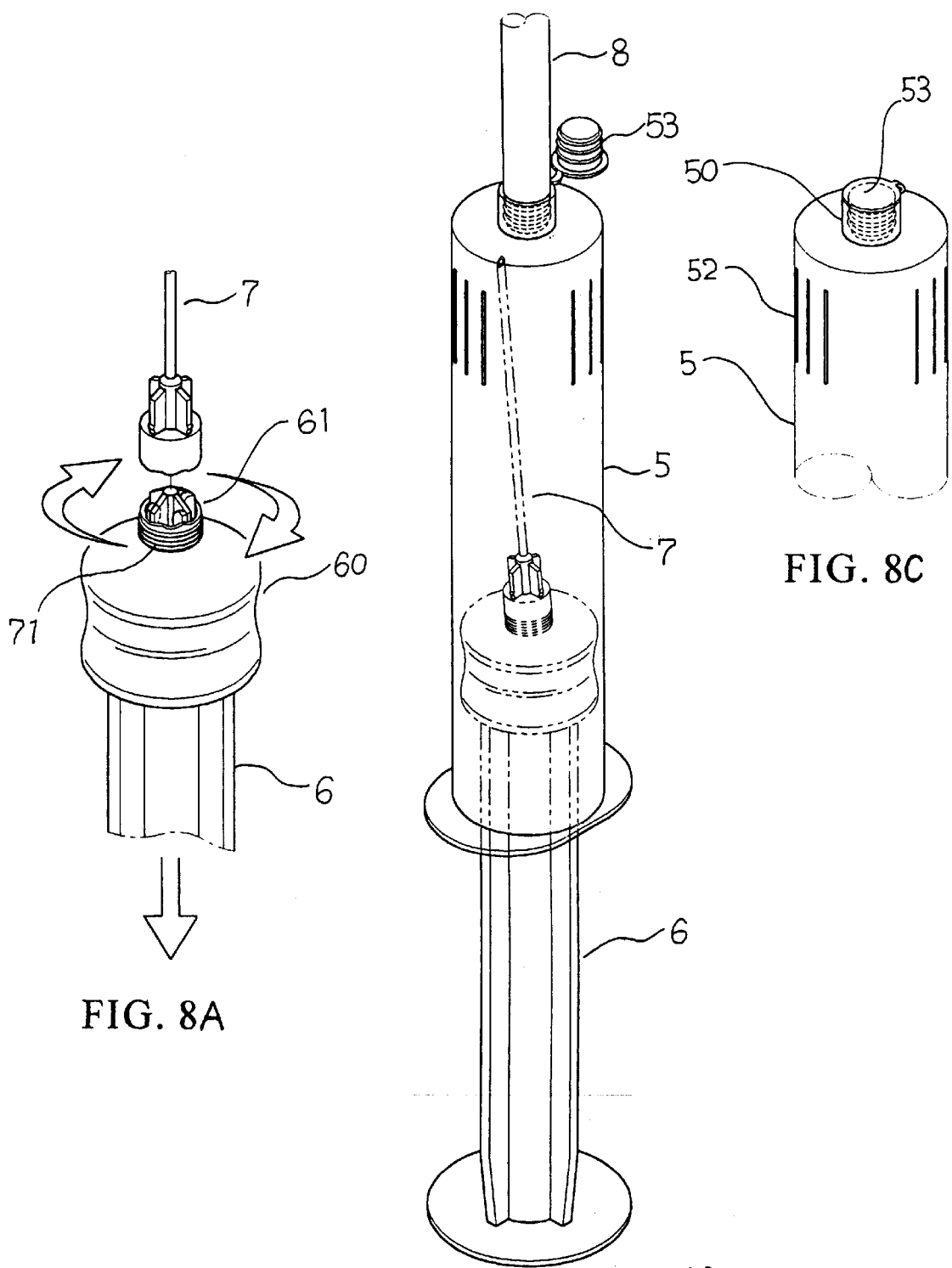
FIGS. 8A, 8B and 8C are serial diagrams showing the withdrawal of a used needle into the container of the safety syringe of the present invention.

Afterwards, the injection rod 6 is continually rotated until the needle 7 disengages from the threaded needle mounting neck 50 and then the injection rod 6 is pulled outwardly so as to withdraw the needle into the container 5 for disposal, as shown in FIGS. 8A, 8B. Then, the lid 53 is engaged with the needle mounting neck 50 to get the container closed, as shown in FIG. 8C. Moreover, to safely confine a disposed needle in the container 50, the needle receiving tube 8 is alternatively engaged with the needle mounting neck 50 with its closed end having a spiral rib 81, better preventing the needle 7 from accidentally sticking out of the needle mounting neck 50.

To make the disposed needle 7 easily lean to one side in the container 5 after it is withdrawn thereinto for preventing the needle 7 from directly sticking out of the needle mounting neck 50 by accident even the lid 53 or needle receiving tube 8 is not engaged with the needle mounting neck 50, the plunger end 61 of the piston head 60 of the injection rod 6 is modified to have only two of the oppositely disposed vertical planes provided with projected spots 62.

It can be clearly realized from the above description that the safety syringe of the present invention can be operated with ease and safety from the beginning to the end and it can be also mass produced economically and sold at a reasonable price.

I claim:

1. A safety syringe for medical injection, comprising a tubular container, an injection rod, a needle and a needle receiving tube; wherein said tubular container has a protruding needle mounting neck at one end and a holding flange at an opposite end;

said protruding needle mounting neck is provided with a lid attached to an edge of said needle mounting neck, and a threaded inner wall for threadingly engaging threads of said needle;

said injection rod has a cross-shaped cross-section;

a rubber piston head provided with a plunger end having a cross-shaped cross-section is disposed at one end of said injection rod;

said plunger end has four vertical plunger planes perpendicular to each other and a boss is provided at an edge of each plane;

a round disc is provided at an opposite end of said injection rod;

said needle has a slantly cut injection hole at one end and an externally threaded cylindrical mounting end at an opposite end, said mounting end being arranged to engage said threaded inner wall of said needle mounting neck of said tubular container;

a protruding block in the same shape as said plunger end and having a cross-shaped cross-section made up of four vertical mounting end planes orthogonal to each other is disposed at a top of said cylindrical mounting end so that said needle can be fixed in said needle receiving tube;

said externally threaded cylindrical mounting end is provided with four symmetrically disposed mounting end lugs on an inner wall thereof, wherein said mounting end lugs are arranged to engagingly fit with said cross-shaped plunger end of said piston head;

said cylindrical mounting end has an inwardly protruding ring adjacent to an edge of said mounting end, said ring being arranged so that said needle is retained by said ring after said bosses are forced past said ring;

said needle receiving tube has a slightly tapered shape and is equipped with a plurality of protrusions in a longitudinal direction and has an open bottom end and a closed top end which is provided with a continuous external spiral rib for engagement with said needle mounting neck of said tubular container;

a peripheral flange is disposed at the open bottom end of said needle receiving tube; and four symmetric receiving tube lugs are disposed inside said receiving tube and near said flange, said receiving tube lugs being arranged to drivingly engage said four vertical mounting end planes of the protruding block disposed at the top of the cylindrical mounting end of said needle, whereby to mount a fresh needle housed in said needle receiving tube onto said tubular container, the opened end of said needle receiving tube is attached to said needle mounting neck and said plunger end of said injection rod is forced into engagement with said cylindrical mounting end of said needle and then said injection rod is rotated continually until said needle is secured by way of its threads to said needle mounting neck of said tubular container; after said needle is secured in place to said container, said needle receiving tube is then removed to expose the secured needle for use; when liquid medicine in said safety syringe runs out through injection step by step and the tubular container is to be disposed of, the container is held with one hand and said injection rod is continued to be pushed with the other hand by way of said round disc, causing said plunger end of said rubber piston head to engage with said mounting end of said needle; said four symmetric vertical planes of said cross-shaped plunger end being limited by said four symmetric semi-circular lugs with the projected spots retained in place by the protruded ring at the same time; afterwards, said injection rod is continually rotated until the needle disengages from said threaded needle mounting neck and then said injection rod is pulled outwardly so as to withdraw the needle into the container for disposal; then, the lid is engaged with said needle mounting neck to get the container closed and to safely confine a disposed needle in said container, said needle receiving tube is alternatively engaged with said needle mounting neck with its closed end having a spiral rib, better preventing a disposed needle from accidentally sticking out of said needle mounting neck.

2. The safety syringe for medical injection as claimed in claim 1, wherein said plunger end of said piston head of said injection rod is modified to have only two of the oppositely disposed vertical planes provided with projecting bosses arranged to make a disposed needle easily lean to one side in said container after it is withdrawn thereinto, thereby preventing the needle from directly sticking out of said needle mounting neck by accident even when said lid or needle receiving tube is not engaged with said needle mounting neck.

3. The safety syringe as claimed in claim 1, wherein said injection rod has a triangular, rectangular or hexagonal cross section.

\* \* \* \* \*